United States Patent
Ichihashi

(10) Patent No.: US 11,202,555 B2
(45) Date of Patent: Dec. 21, 2021

(54) OPTICAL ADAPTER FOR AN ENDOSCOPE

(71) Applicant: OLYMPUS CORPORATION, Tokyo (JP)

(72) Inventor: Masaki Ichihashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 874 days.

(21) Appl. No.: 15/966,205

(22) Filed: Apr. 30, 2018

(65) Prior Publication Data

US 2018/0242823 A1 Aug. 30, 2018

Related U.S. Application Data

(63) Continuation of application No. PCT/JP2016/085727, filed on Dec. 1, 2016.

(30) Foreign Application Priority Data

Dec. 17, 2015 (JP) .............................. JP2015-246044

(51) Int. Cl.
*A61B 1/00* (2006.01)
*G02B 23/24* (2006.01)
*G02B 23/26* (2006.01)

(52) U.S. Cl.
CPC ...... *A61B 1/00126* (2013.01); *A61B 1/00096* (2013.01); *G02B 23/243* (2013.01);
(Continued)

(58) Field of Classification Search
CPC .................... A61B 1/00096; G02B 23/2415
See application file for complete search history.

(56) References Cited

U.S. PATENT DOCUMENTS 5,971,915 A 10/1999 Yamamoto et al.
6,361,491 B1 * 3/2002 Hasegawa .......... A61B 1/00096
348/45

(Continued)

FOREIGN PATENT DOCUMENTS

JP H09-127435 A 5/1997
JP H11-006967 A 1/1999

(Continued)

OTHER PUBLICATIONS

International Search Report dated Jan. 24, 2017 issued in PCT/JP2016/085727.

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

This optical adapter for an endoscope includes a plurality of incident optical systems eccentrically disposed with each other, an optical axis of each of the plurality of incident optical systems being spaced away from an axis of the optical adapter for an endoscope with an interval; a brightness stop including a plurality of apertures corresponding to the plurality of incident optical systems respectively; a relay lens configured to relay incident light entering each of the plurality of incident optical systems to the corresponding aperture; and a distal light-shielding portion which is disposed more distally than the relay lens, wherein the plurality of incident optical systems, the relay lens, and the brightness stop are disposed in this order from a distal end side toward a proximal end side of the optical adapter for an endoscope along an incident direction of the incident light.

9 Claims, 8 Drawing Sheets

(52) U.S. Cl.
CPC ..... *G02B 23/2415* (2013.01); *G02B 23/2446* (2013.01); *G02B 23/2461* (2013.01); *G02B 23/2469* (2013.01); *G02B 23/26* (2013.01)

(56) References Cited

U.S. PATENT DOCUMENTS

| | | | | |
|---|---|---|---|---|
| 2002/0161278 | A1* | 10/2002 | Nakamura | A61B 1/00096 600/111 |
| 2003/0125608 | A1* | 7/2003 | Igarashi | A61B 1/00096 600/166 |

FOREIGN PATENT DOCUMENTS

| | | |
|---|---|---|
| JP | 2001-147382 A | 5/2001 |
| JP | 2014-160240 A | 9/2014 |

\* cited by examiner

OPTICAL ADAPTER FOR AN ENDOSCOPE

This application is a continuation application based on a PCT International Application No. PCT/JP2016/085727, filed on Dec. 1, 2016, whose priority is claimed on a Japanese Patent Application No. 2015-246044, filed on Dec. 17, 2015. The contents of both of the PCT International Application and the Japanese Patent Application are incorporated herein by reference.

BACKGROUND OF THE INVENTION

Field of the Invention

The present invention relates to an optical adapter for an endoscope.

Description of Related Art

Conventionally, in order to observe an inside of a detection object such as the inside of a mechanical structure in the industrial field, and an inner cavity of a patient in the medical filed, an endoscope is widely used. Such an endoscope has an elongated insertion portion which is inserted into the inside of the detection object. An observation means is provided at a distal end of the insertion portion. The insertion portion has a flexible bending portion and a rigid distal end portion at the distal end side thereof. By inserting the insertion portion to the inside of the detection object and then using an operation portion disposed at a proximal end side thereof to bend the bending portion, a direction of the distal end of the endoscope is adjusted such that it is possible to observe a desired observation position inside the detection object by using the observation means.

In such type of endoscopes, an endoscope having two optical systems provided on the left side and the right side in the rigid distal end portion respectively is known, wherein the endoscope is configured to measure a shape of an observation object by using the parallax between the two optical systems. In such endoscope, it is general to removably attach a stereo optical adapter to the endoscope for corresponding to various situations such as different observation directions, different observation depths, and different view angles.

With regard to such optical adapter removably attached to the endoscope, since it is necessary to determine the mostly suitable brightness for each of a plurality of different optical adapters, a brightness stop (aperture stop, AS) is provided in each optical adapter. Generally, with regard to such optical adapter, one brightness stop is provided for two of the left and right optical systems for forming images of the left and right optical systems.

However, in a situation in which only one brightness stop is provided in the conventional optical adapter, travel lengths of light rays passing through the left and right optical systems to reach the image sensor become long such that it is necessary to configure a rigid region of the distal end portion of the endoscope (a rigid distal end portion) to be long. Details will be described below. In order to shorten the length of the rigid distal end portion for making the insertion into the detection object to be easier, it is proposed to configure an endoscope having two brightness stops corresponding to the left and right optical systems respectively. In the endoscope having two brightness stops, compared to the endoscope having only one brightness stop, leakage of light on the left and right sides may occur due to the unnecessary light which pass through the left and right optical systems undesirably. In order to solve this problem, an endoscope disclosed in Japanese Unexamined Patent Application, First Publication No. 2014-160240 and an endoscope disclosed in Japanese Unexamined Patent Application, First Publication No. H9-127435 are proposed.

Specifically, an imaging portion of a stereoscopic endoscope disclosed in Japanese Unexamined Patent Application, First Publication No. 2014-160240 is configured to have two imaging optical systems, a lens frame holding the two imaging optical systems, a shielding plate separating light rays on the left side and the right side that pass through the two imaging optical systems respectively, and two filter groups having infrared cut filters and the like. In an optical system disclosed in Japanese Unexamined Patent Application, First Publication No. H9-127435, the possibility of incident of the flare light into a space between a left lens group and a right lens group is reduced by providing a shielding member between the left lens group and the right lens group.

SUMMARY OF THE INVENTION

According to a first aspect of the present invention, an optical adapter for an endoscope configured to be removably attached to a distal end of an insertion portion of an endoscope, wherein the optical adapter for an endoscope includes a plurality of incident optical systems which are eccentrically disposed with each other, an optical axis of each of the plurality of incident optical systems being spaced away from an axis of the optical adapter for an endoscope with an interval; a brightness stop which includes a plurality of apertures, the plurality of apertures corresponding to the plurality of incident optical systems respectively; a relay lens which is configured to relay incident light entering each of the plurality of incident optical systems to the corresponding aperture among the plurality of apertures of the brightness stop; and a distal light-shielding portion which is disposed more distally than the relay lens, wherein the plurality of incident optical systems, the relay lens, and the brightness stop are disposed in this order from a distal end side toward a proximal end side of the optical adapter for an endoscope along an incident direction of the incident light.

According to a second aspect of the present invention, the optical adapter for an endoscope according to the first aspect may further include a distal flare-cut stop which is disposed more distally than the relay lens, wherein the distal light-shielding portion is disposed at the distal flare-cut stop.

According to a third aspect of the present invention, in the optical adapter for an endoscope according to the first aspect, the distal light-shielding portion may be formed on a distal surface of the relay lens.

According to a fourth aspect of the present invention, the optical adapter for an endoscope according to the first aspect may further include a proximal light-shielding portion which is disposed more proximally than the relay lens.

According to a fifth aspect of the present invention, the optical adapter for an endoscope according to the fourth aspect may further include a distal flare-cut stop which is disposed more distally than the relay lens, and a proximal flare-cut stop which is disposed more proximally than the relay lens, wherein the distal light-shielding portion is disposed at the distal flare-cut stop, and the proximal light-shielding portion is disposed at the proximal flare-cut stop.

According to a sixth aspect of the present invention, in the optical adapter for an endoscope according to the fourth aspect, the distal light-shielding portion may be formed on a distal surface of the relay lens, and the proximal light-shielding portion may be formed on a proximal surface of the relay lens.

According to a seventh aspect of the present invention, the optical adapter according to the first aspect may further include a lens frame which is configured to hold the plurality of incident optical systems; and an adapter main body which is configured to hold the relay lens, wherein the lens frame is abutted by the adapter main body such that the lens frame and the adapter main body are engaged with each other to determine positions of the plurality of incident optical systems with respect to the relay lens.

According to an eighth aspect of the present invention, in the optical adapter for an endoscope according to the first aspect, the relay lens may be a cemented lens which is formed by combining a distal lens and a proximal lens.

DETAILED DESCRIPTION OF THE INVENTION

First Embodiment

Figure 1:
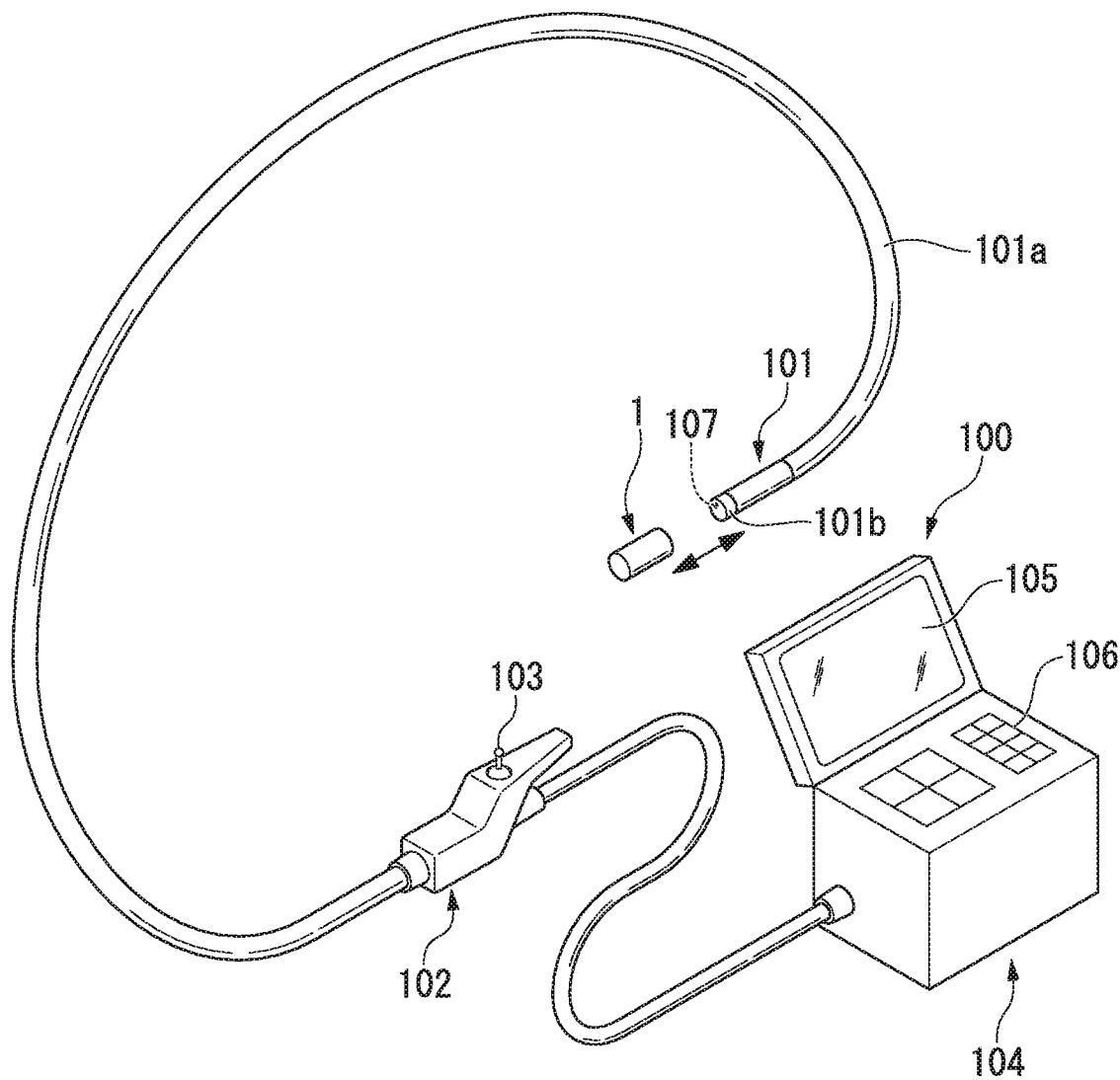
FIG. 1 is a view showing an optical adapter for an endoscope according to a first embodiment of the present invention and an endoscope to which the optical adapter for an endoscope is attached.

An optical adapter 1 for endoscope according to a first embodiment of the present invention will be described. FIG. 1 is a view showing the optical adapter 1 for endoscope (hereinafter described as "adapter") and an endoscope 100 to which the adapter 1 is attached.

The endoscope 100 has a conventional configuration. As shown in FIG. 1, the endoscope 100 has an elongated endoscope insertion portion 101, an operation portion 102, and an operation portion main body 104. The endoscope insertion portion 101 has an observation optical system 107 at a distal end thereof. The operation portion 102 has a joystick 103, a display portion 105, and an operation panel 106, and the operation portion 102 is connected with the endoscope insertion portion 101. The joystick 103 is an operation member for operating the endoscope insertion portion 101. The display portion 105 displays an image of the inside of the detection object acquired by the endoscope insertion portion 101. The operation panel 106 is provided for performing various operations of the endoscope 100. The operation portion main body 104 is connected to a battery or an AC power supply which are not shown.

Figure 2:
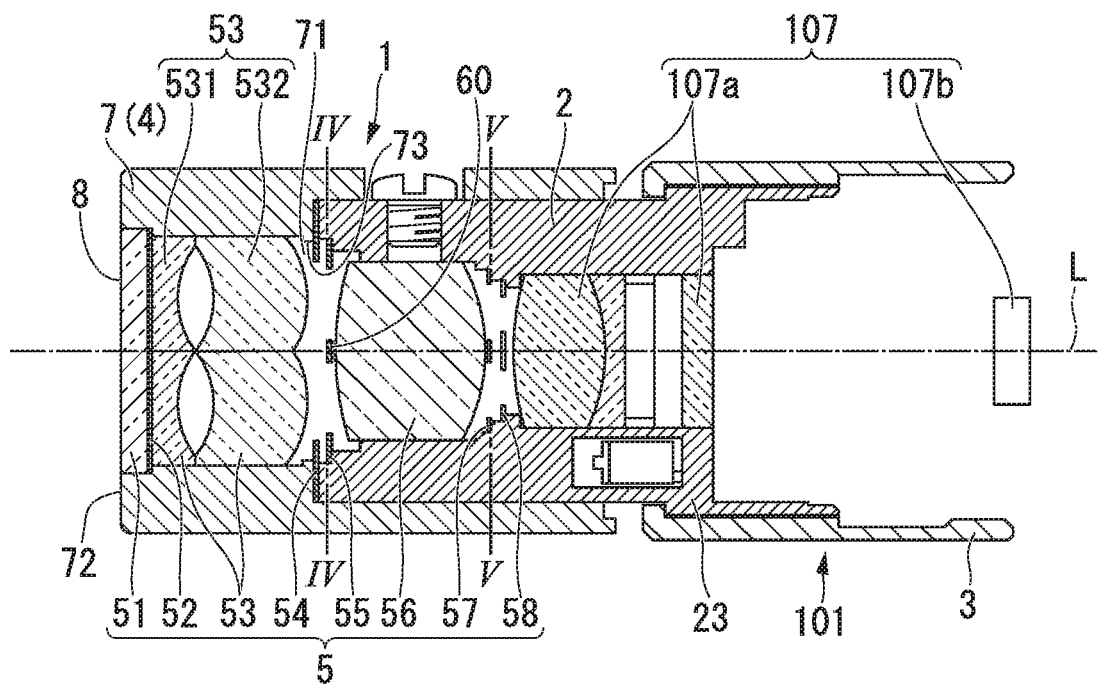
FIG. 2 is a sectional view showing a configuration of the optical adapter for an endoscope according to the first embodiment.
Figure 3:
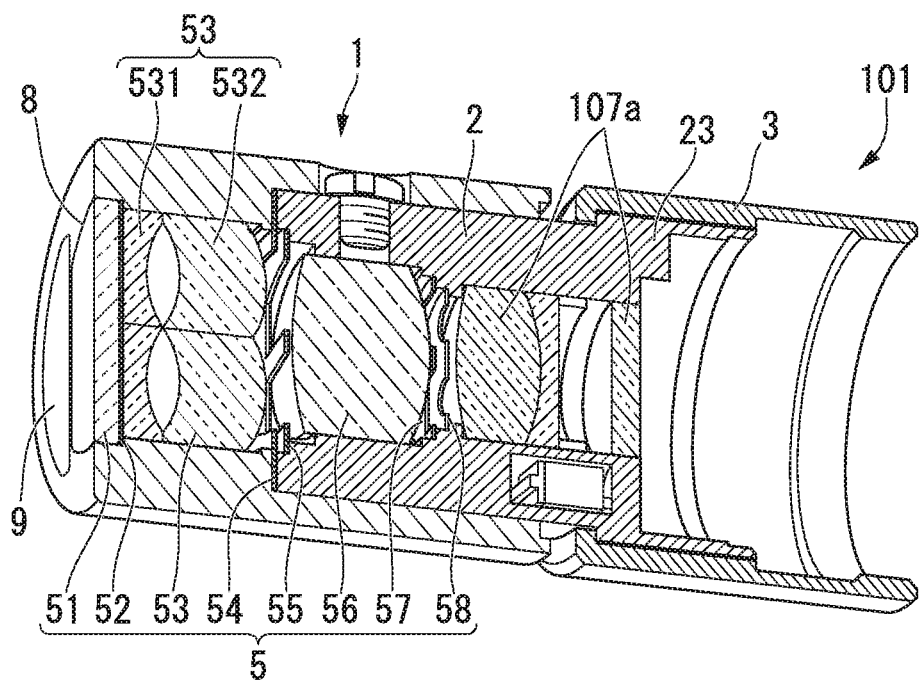
FIG. 3 is a perspective view showing the optical adapter for an endoscope according to the first embodiment.

FIG. 2 is a sectional view of the adapter 1 which is attached to a distal end of the endoscope insertion portion 101, and FIG. 2 is a sectional view taken along a longitudinal axis L of the adapter 1. FIG. 3 is a perspective view of the adapter 1.

As shown in FIG. 2 and FIG. 3, the adapter 1 has an adapter main body (main body) 2, a hood 3, a lens holding member (holding member) 4, an adapter optical system 5, a light-guide 6 (See FIG. 4), and a cover 7. The adapter 1 is a direct-view type of stereo optical adapter for an endoscope. The adapter 1 has an observation surface 8 along the longitudinal axis L of the adapter 1. In the description hereinafter, a side at which the observation surface 8 is disposed is defined as a distal side (the left side in FIG. 2), and a side at which the endoscope insertion portion 101 is disposed is defined as a proximal side (the right side in FIG. 2). Also, a direction to which the observation surface 8 is parallel, to which the longitudinal axis L of the adapter 1 is orthogonal, and in which a pair of eccentrical lens 53 which will be described below are disposed is defined as a width direction (the upper direction and the lower direction in FIG. 2).

The adapter optical system 5 according to the present embodiment has a cover glass 51, a visual-field stop (mask) 52, the pair of eccentrical lens (incident optical system) 53, a focus adjustment sheet 54, a distal flare-cut stop 55, a relay lens 56, a proximal flare-cut stop 57, and a brightness stop 58 in this order from the distal side thereof.

The cover glass 51 is a glass plate for protecting the adapter optical system 5 and the cover glass 53 has a conventional configuration. The visual-field stop 52 is disposed between the cover glass 51 and the pair of eccentrical lens 53. The visual-field stop 52 is configured to shield a part of the unnecessary light that enters the adapter optical system 5.

The pair of eccentrical lens 53 are disposed side by side in the width direction such that optical axes of the pair of eccentrical lens 53 are parallel to each other. More specifically, the pair of eccentrical lens 53 are disposed side by side in the width direction of the adapter 1 such that the optical axis of each eccentrical lens 53 is spaced away from the optical axis of the adapter 1 with an interval. In the present embodiment, each of the pair of eccentrical lens 53 is configured by a distal lens 531 and a proximal lens 532.

The focus adjustment sheet 54 is configured to be sandwiched between the main body 2 and the lens holding member 4, and the focus adjustment sheet 54 is configured to compensate various deviations of the optical characteristic values of the adapter optical system 5 due to manufacturing error of each component of the adapter optical system 5. The focus adjustment sheet 54 is preferably configured by multiple pieces of sheets with different thickness.

The relay lens 56 is configured to relay the incident light guided by the pair of eccentrical lens 53 to the lens disposed at the distal side of the endoscope insertion portion 101. The optical characteristic of the relay lens 56 can be suitably determined to fulfil the desirable optical characteristic of the adapter 1.

The distal flare-cut stop 55 is disposed at a center part of the distal side of the relay lens 56. The proximal flare-cut stop 57 is disposed at a center part of the proximal side of the relay lens 56. As described below, the distal flare-cut stop 55 and the proximal flare-cut stop 56 are configured to shield the unnecessary light that can enter the brightness stop 58 for preventing the generation of flare. Here, the center part of the distal side of the relay lens 56 refers to a region which is more distal than the relay lens 56 including the vicinity of the optical center of the relay lens 56. Similarly, the center part of the proximal side of the relay lens 56 refers to a region which is more proximal than the relay lens 56 including the vicinity of the optical center of the relay lens 56.

The brightness stop 58 is disposed more proximally than the relay lens 56. In the brightness stop 58, a pair of apertures 59 (See FIG. 5) are formed at positions spaced away from a center of the brightness stop 58 with an interval respectively, wherein the pair of apertures 59 correspond to the pair of eccentrical lens 53 respectively. The incident light which is guided by the relay lens 56 is furtherly guided to pass through the pair of apertures 59 and the incident light is then guided to another lens disposed at the distal end of the endoscope insertion portion 101. The pair of apertures 59 disposed at the brightness stop 58 are formed to have circle shapes respectively to collect the same amount of the incident light in all of the directions guided by the relay lens 56.

Figure 5:
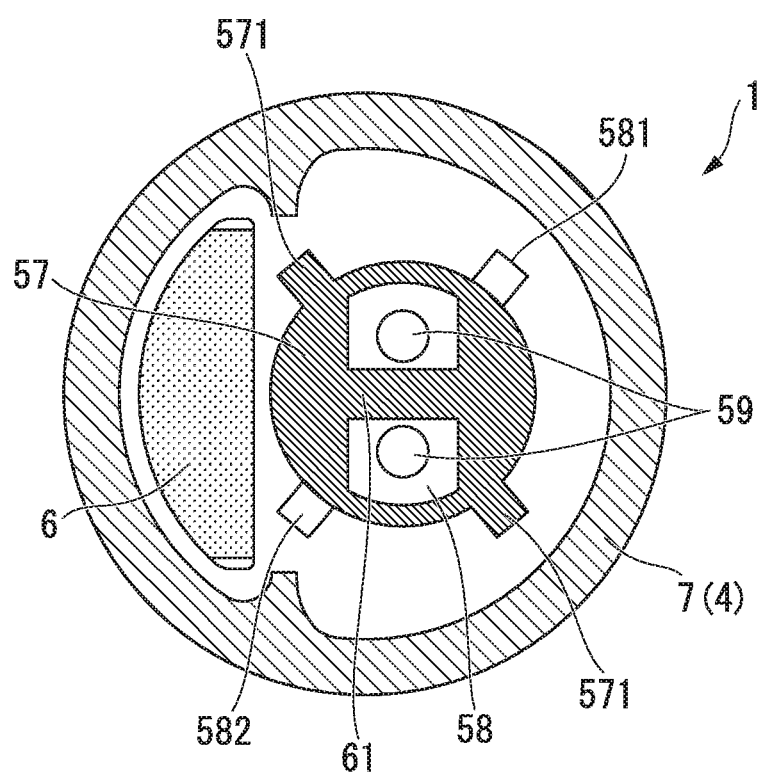
FIG. 5 is a V-V line sectional view of the FIG. 2.

As shown in FIG. 5, two projections are formed as a positioning portion 581 in a circumferential direction of an outward circumferential peripheral of the brightness stop 58. The brightness stop 58 is fixed to the main body 2 by the positioning portion 581 such that a rotation of the brightness stop 58 about the longitudinal axis L of the adapter 1 is restricted.

The lens holding member 4 is a lens frame configured to hold the cover glass 51, the visual-field stop 52, and the pair of eccentrical lens 53 of the adapter optical system 5. The main body 2 is provided to hold the distal flare-cut stop 55, the relay lens 56, the proximal flare-cut stop 57, and the brightness stop 58 of the adapter optical system 5. The main body 2 is abutted by the lens holding member 4 such that the main body 2 and the lens holding member 4 are engaged with each other, wherein the focus adjustment sheet 54 with a thickness for suitably compensating the optical characteristic of the adapter optical system 5 is sandwiched between the main body 2 and the lens holding member 4. For example, the optical characteristic of the adapter optical system 5 can be considered as the focusing characteristic or the like. With such a configuration, as shown in FIG. 3, a predetermined inter-surface distance between proximal optical surfaces of the pair of eccentrical lens 53 and distal optical surface of the relay lens 56 can be defined and determined.

The hood 3 is connected to a proximal end portion of the main body 2, and the hood 3 has a substantial cylindrical shape. The hood 3 and the main body 2 are disposed coaxially with each other. The hood 3 is connected with the main body 2 to be rotatable about the center axis of the main body 2 with respect to the main body 2.

As shown in FIG. 2, the cover 7 is disposed in the distal end portion of the adapter 1, and the cover 7 has a lumen 71 formed inside. The lumen 71 extends from a proximal end 71 to a distal end surface 73 along the longitudinal axis L.

The lumen 71 is configured such that the holding member 4, the light-guide 6 (see FIG. 7), and the illumination cover glass 9 (see FIG. 7) are accommodated inside the lumen 71.

The light-guide 6 is configured to guide illumination light from a light source (not shown) disposed at the proximal end side of the endoscope 100 to the distal side of the adapter 1. The light-guide 6 is configured to irradiate the illumination light through the illumination cover glass 9 (see FIG. 7) to illuminate the observation region of the endoscope 100, wherein the illumination cover glass 9 is disposed more distally than the light-guide 6 in the direction of longitudinal axis L.

Figure 4:
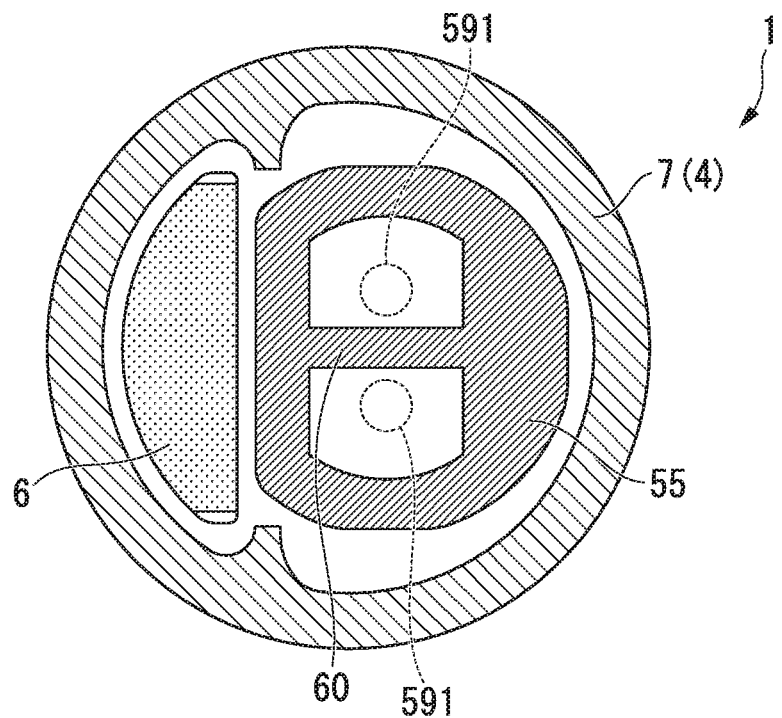
FIG. 4 is an IV-IV line sectional view of the FIG. 2.

Next, the distal flare-cut stop 55 and the proximal flare-cut stop 57 of the adapter 1 according to the present embodiment will be described as the characteristic part of the present invention in detail. FIG. 4 is an IV-IV line sectional view of FIG. 2, and FIG. 4 is a plan view showing a distal light-shielding portion 60. FIG. 5 is a V-V line sectional view of FIG. 2, and FIG. 5 is a plan view showing a proximal light-shielding portion 61. For convenience of description, in FIGS. 4 and 5, the width directions are shown as the upper and lower directions.

As shown in FIG. 4, the distal flare-cut stop 55 is disposed at the center part of the distal side of the relay lens 56 of the adapter 1 according to the present embodiment. Generally, with regard to a conventional optical adapter for an endoscope having a pair of eccentrical lens, an image (a flare) due to the incident light guided by the pair of eccentrical lens is occasionally formed on an image sensor. In the adapter 1 according to the present embodiment, the distal flare-cut stop 55 is configured to shield part of the unnecessary light which has possibility to generate the flare among the incident light from the pair of eccentrical lens 53, and thus to improve the quality of the image formed on the image sensor.

In FIG. 4, a pair of virtual apertures 591 corresponding to the pair of apertures 59 formed in the brightness stop 58 respectively are shown. The distal flare-cut stop 55 according to the present embodiment is configured to surround the pair of virtual apertures 591. In the distal flare-cut stop 55, a distal light-shielding portion 60 with a rectangle shape having a suitable uniform width (a dimension in the width direction of the adapter 1) is disposed between the pair of virtual apertures 591. The distal light-shielding portion 60 is configured to shield part of the incident light guided by each of the pair of eccentrical lens 53, that is, the undesirable leak light from each of the pair of eccentrical lens 53 to the pair of apertures 59 of the brightness stop 58.

As shown in FIG. 4, the distal flare-cut stop 55 according to the present embodiment is configured to have several D-cut processing portions such that the distal flare-cut stop 55 has a substantial D shape. The distal flare-cut stop 55 is fixed to the main body 2. Due to the several D-cut processing portions, rotation of the distal flare-cut stop 55 about the longitudinal axis L of the adapter 1 is restricted.

As shown in FIG. 5, the proximal flare-cut stop 57 is disposed at the center part of the proximal side of the relay lens 56 of the adapter 1. The proximal flare-cut stop 57 according to the present embodiment has two projections formed as a positioning portion 571 in a circumferential direction of an outward circumferential peripheral of the proximal flare-cut stop 57. Due to the positioning portion 571, the proximal flare-cut stop 57 is fixed to the main body 2 and thus a rotation of the proximal flare-cut stop 57 about the longitudinal axis L of the adapter 1 is restricted.

The proximal flare-cut stop 57 according to the present embodiment is configured to surround the pair of apertures 59 formed in the brightness stop 58. In the proximal flare-cut stop 57, a proximal light-shielding portion 61 with a rectangle shape having a suitable uniform width (a dimension in the width direction of the adapter 1) is disposed between the pair of apertures 59.

With regard to the adapter for endoscope, generally, the light beam is broadest at a position where the brightness stop of the optical system is disposed, and the light beam becomes narrower as the distance to the brightness stop increases. Accordingly, the width of the proximal light-shielding portion 61 is determined to be substantially the same or larger than the smallest dimension of the pair of apertures 59 of the corresponding brightness stop 58, and the width of the proximal light-shielding portion 61 is determined to prevent the desired light from being shielded. As a result, the leak light from the pair of eccentrical lens 53 to the brightness stop 58 can be shielded.

Next, effects of shielding the leak light via the pair of apertures 59 of the brightness stop 58 using the distal light-shielding portion 60 and the proximal light-shielding portion 61 according to the present embodiment will be described.

Figure 10:
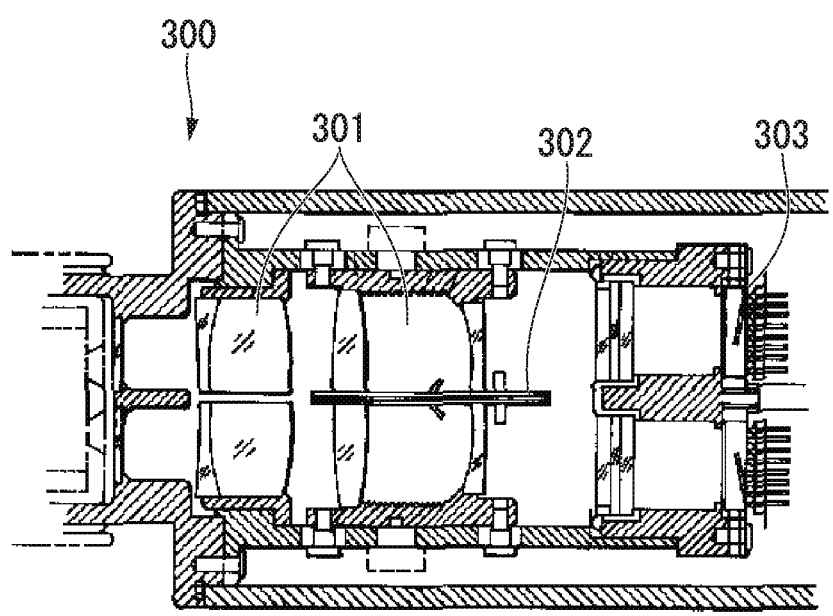
FIG. 10 is a view showing a configuration of a conventional endoscope device.

FIG. 10 shows a configuration of an optical adapter for an endoscope 300 disclosed in Japanese Unexamined Patent Application, First Publication No. H9-127435. The optical adapter for an endoscope 300 has a brightness stop having two apertures. This optical adapter for an endoscope 300 has a light-shielding plate 302 which is sandwiched between left and right eccentrical lens 301.

When such an endoscope is assembled, it is necessary to perform optical adjustment such as focus adjustment for achieving the desirable optical characteristic of the endoscope in consideration of manufacturing variations of each element. Generally, during the optical adjustment, the distance between the relay lens and the eccentrical lens decreases when the relay lens is adjusted by being moved distally, and the distance between the relay lens and the eccentrical lens increases when the relay lens is adjusted by being moved proximally.

Figure 11A:
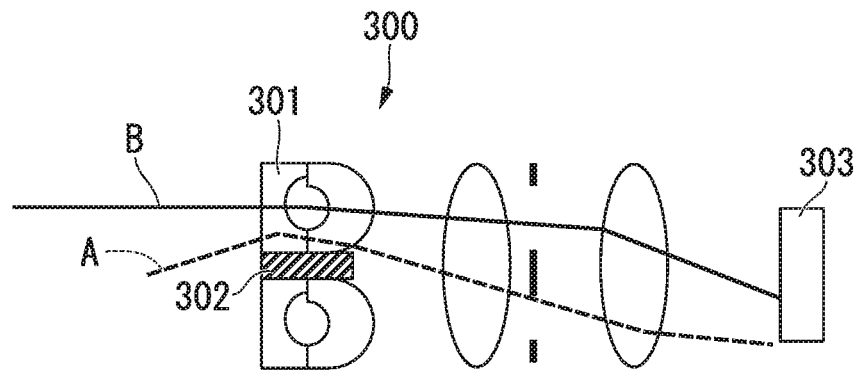
FIG. 11A is a view showing a light-shielding process in the conventional endoscope device.
Figure 11B:
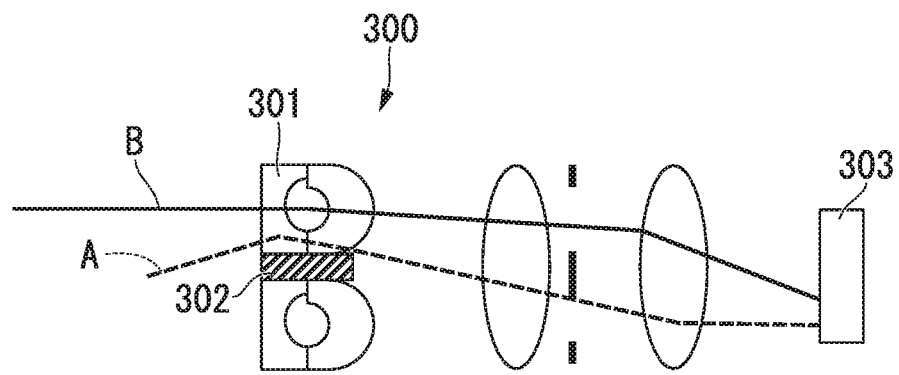
FIG. 11B is a view showing the light-shielding process in the conventional endoscope device.
Figure 11C:
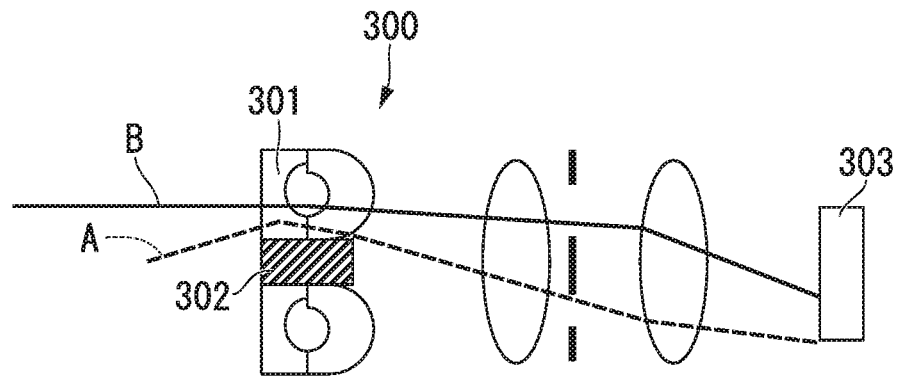
FIG. 11C is a view showing the light-shielding process in the conventional endoscope device.

In FIGS. 11A to 11C, an optical path represent by a solid line B shows an optical path of a principal ray passing through the optical system of the optical adapter (adapter) 300 for endoscope. An optical path represent by a broken line A shows an optical path of the leak incident light that is possible to enter the optical system of the optical adapter 300 for endoscope. When the relay lens (not shown) is adjusted by being moved distally, that is, in the situation when the distance between the relay lens and the eccentrical lens 301 decreases, as shown in FIG. 11A, since the light-shielding plate 302 is configured to shield part of the optical path of the leak incident light A entering the brightness stop, an incident angle of the leak incident light A entering the brightness stop increases. As a result, the leak incident light A does not form an image on an image sensor 303 disposed at the distal end of the insertion portion of the endoscope. However, as shown in FIG. 11B, when the relay lens is adjusted by being moved proximally, that is, in the situation when the distance between the relay lens and the eccentrical lens 301 increases, the incident angle of the leak incident light A enterable to the brightness stop decreases. Accordingly, the leak incident light A passes through the relay lens, the brightness stop, and the distal-end lens of the endoscope to form an image on the image sensor 303 disposed at the distal end of the insertion portion of the endoscope. As a result, the undesirable image, that is, the flare is occurred and detected by the image sensor 303. In order to suppress the occurrence of the flare, as shown in FIG. 11C, a solution of increasing the thickness of the light-shielding plate 302 is proposed. However, according to such a configuration, an outer diameter of the optical adapter 300 for endoscope increases and an insertion flexibility to the detection object is impaired.

Figure 6A:
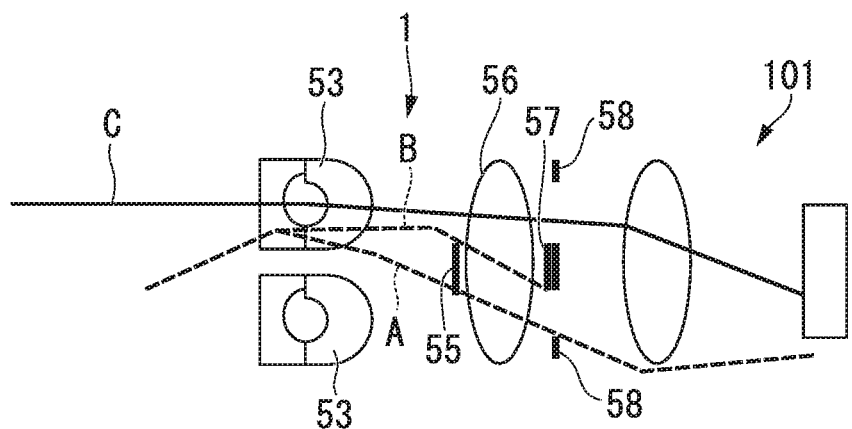
FIG. 6A is a schematic diagram showing a light-shielding principle of the optical adapter for an endoscope according to the first embodiment.
Figure 6B:
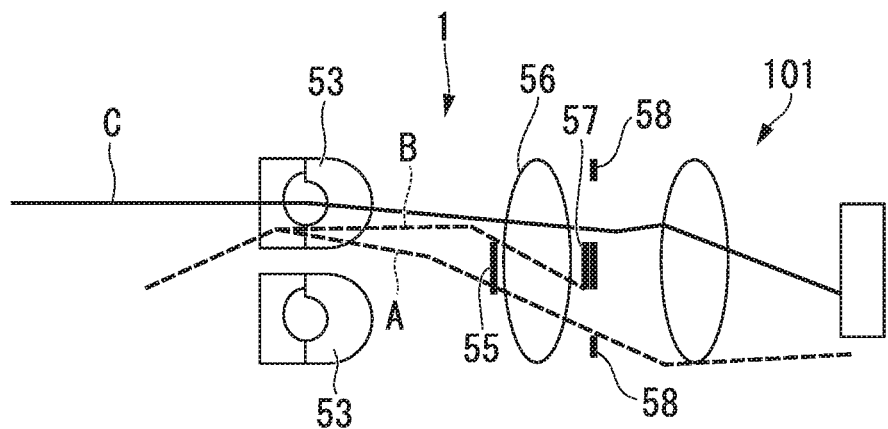
FIG. 6B is a schematic diagram showing a light-shielding principle of the optical adapter for an endoscope according to the first embodiment.

As described above, the adapter 1 according to the present embodiment is configured to include both of the distal flare-cut stop 55 having the distal light-shielding portion 60 disposed at the center part of the distal side of the relay lens 56, and the proximal flare-cut stop 56 having the proximal light-shielding portion 61 disposed at the center part of the proximal side of the relay lens 56. The optical path of the adapter 1 according to the present embodiment is shown in FIGS. 6A and 6B. A solid line C shows the optical path of a principal ray through the adapter optical system 5. Similar to the description above, broken lines A and B show the possible optical path of the leak incident light entering the adapter optical system 5. As shown in FIG. 6B, when the relay lens 56 is adjusted by being moved proximally in order to perform the focus adjustment of the adapter 1 according to the present embodiment, that is, when the distance between the relay lens and the eccentrical lens 53 increases, the width of the distal light-shielding portion 60 is determined such that the leak incident light A cannot form the image on the image sensor through the eccentrical lens 53, the distal flare-cut stop 55, the relay lens 56, the brightness stop 58, and the distal-end lens of the insertion portion of the endoscope. On the other hand, as described above, the width of the proximal light-shielding portion 61 is determined to be substantially the same or larger than the smallest dimension of each aperture 59 of the corresponding brightness stop 58, thus the leak incident light B occurred from the eccentrical lens 53 to the aperture 59 of the brightness stop 58 can be shielded. Furthermore, the broken lines A and B represent the limit positions of the leak incident light possible to enter the relay lens 56. Accordingly, by the distal light-shielding portion 60 and the proximal light-shielding portion 61 according to the present embodiment, the light beam of the leak incident light possible to enter the relay lens 56 can be suitably shielded. By disposing the proximal light-shielding portion 61 proximally than the relay lens 56 at a position as close as possible to the relay lens 56, the desirable light beam can be narrowed such that the width of the proximal light-shielding portion 61 can be increased and the leak incident light B can be more preferably shielded.

In the adapter 1 according to the present embodiment, the relay lens 56, the distal flare-cut stop 55, the proximal flare-cut stop 57, and the brightness stop 58 are held by the main body 2. That is, in the adapter 1 according to the present embodiment, a positional relationship among the distal flare-cut stop 55, the proximal flare-cut stop 56, and the brightness stop 58 are fixed. In the situation when the relay lens 56 is adjusted by being moved distally during the focus adjustment of the adapter 1, the leak incident light at least has to be incident at a further smaller incident angle than the incident angle of the leak incident light as shown in FIG. 6B in order to form the image on the image sensor disposed at the distal end of the insertion portion of the endoscope. However, as shown in FIG. 6A, in the situation when the relay lens 56 is adjusted by being moved distally, the distance between the pair of the eccentrical lens 53 and the relay lens 56 decreases such that the incident angle of the leak incident light entering the relays lens 56 increases. Accordingly, as shown in FIG. 6A, the leak incident light that is possible to enter the relay lens 56 can be suitably shielded by the distal light-shielding portion 60 and the proximal light-shielding portion 61 of the adapter 1 according to the present embodiment.

Next, an example of attaching the adapter 1 at the distal end of the endoscope insertion portion 101 will be described.

A user inserts the distal end of the endoscope insertion portion 101 from the proximal end side of the hood 3, and the user rotates the hood 3 while holding the cover 7 to insert the distal end of the endoscope insertion portion 101 into a proximal-end opening 23 of the main body 2 until an observation window of the endoscope insertion portion 101 contacts with an observation window of the adapter optical system 5. By the operation described above, the hood 3 is engaged with the endoscope insertion portion 101, and an optical axis of the observation optical system 107 is coincided with the axes of the brightness stop 58, the relay lens 56, and the focus adjustment sheet 54 of the adapter optical system 5. In this state, the adapter 1 is fixed at a predetermined position with respect to the endoscope insertion portion 101 in the direction along the longitudinal axis L. At the meantime, an alignment of an insertion portion light-guide (not shown) and the light-guide 6 of the adapter 1 is performed.

Figure 7:
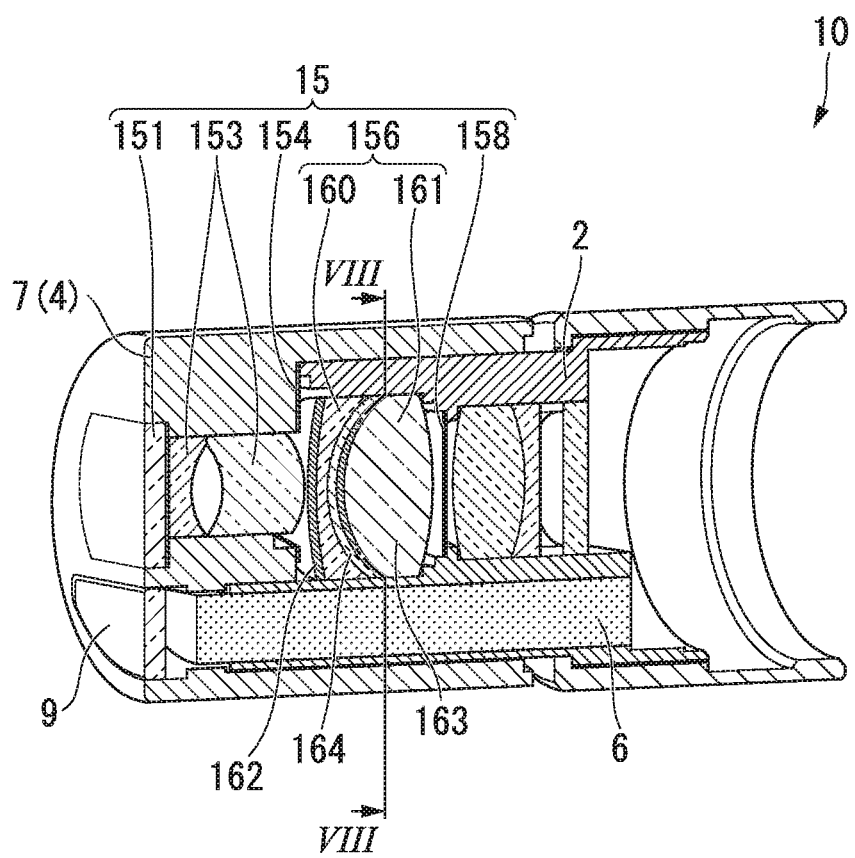
FIG. 7 is a view showing a configuration of an optical adapter for an endoscope according to a second embodiment of the present invention.

When the user turns on the illumination at the operation portion main body 104, the light is transmitted from the insertion portion light-guide to the light-guide 6 and the light is irradiated from the illumination cover glass 9 (see FIG. 7). By the operation at the operation portion main body 104, the image of the detection object in the view-field of the observation surface 8 is transmitted to the solid image sensor 107*b* (see FIG. 2) to form an image of the detection object. The image of the detection object is processed at the solid image sensor 107*b* to be displayed at the display portion 105.

When the observation of the detection object is finished and the variation of the adapter necessary for the observation of the detection object is exchanged, the user rotates the hood 3 in a reverse direction with respect to the rotation direction of the hood 3 when the user attaches the adapter 1 while holding the cover 7 to remove the adapter 1 from the distal end of the endoscope insertion portion 101. As description above, the adapter 1 is configured to be removably attached to the distal end of the endoscope insertion portion 101.

The adapter 1 according to the present embodiment is configured such that, the distal flare-cut stop 55 having the distal light-shielding portion 60 is disposed at the center part of the distal end side of the relay lens 56 disposed at the distal side of the brightness stop 58, and the proximal flare-cut stop 57 having the proximal light-shielding portion 61 is disposed at the center part of the proximal end side of the relay lens 56. Accordingly, the leak incident light is prevent from passing through the relay lens 56 to form the image on the image sensor at the distal end portion of the endoscope 100, and thus it is possible to prevent the generation of the flare.

The adapter 1 according to the present embodiment is not necessary to be configured with a conventional light-shielding plate between the pair of the eccentrical lens 53. Accordingly, it is easy to widening the width of the distal light-shielding portion 60 disposed at the distal flare-cut stop 55 without enlarging the outer diameter of the adapter 1, and thus the leak incident light can be suitably shielded.

In the conventional stereo optical adapter, a common aperture corresponding to the pair of the left and right optical systems is disposed at the center part of the brightness stop. Accordingly, in order to form an image on the image sensor, the angle at which the incident light is refracted by the relay lens is large. That is, in a situation of being configured with the same relay lens, compared to the conventional stereo optical adapter, the adapter 1 according to the present embodiment is configured to have the pair of the apertures 59 corresponding to the pair of the left and right eccentrical lens 53 respectively, and thus the refraction angle of the incident light can be decreased. In other words, the adapter 1 according to the present embodiment is configured to be capable of shortening the length of the optical path of the incident light to form the image on the image sensor. Accordingly, the adapter 1 according to the present embodiment can shorten the length of the rigid portion accommodating the adapter optical system 5.

The adapter 1 according to the present embodiment is not necessary to be configured with a conventional light-shielding plate between the pair of the eccentrical lens 53. Accordingly, the diameter of each eccentrical lens 53 can be enlarged without enlarging the outer diameter of the optical adapter 1. As a result, lengths of a left base line and a right base line of the adapter optical system 5 can be increased and thus the measurement precision can be improved. Otherwise, an angle of view in the width direction of the adapter 1 can be enlarged, and thus a suitable observation image can be achieved. Also, since a common imaging area between a left image and a right image formed on the solid image sensor 107*b* by the pair of left and right eccentrical lens 53 respectively increases, a possible measurement range can be enlarged. Also, since the light-shielding plate is not included, a number of elements of the adapter 1 is reduced, and the holding member 4 as the lens frame, the main body 2 and each lens are easy to be manufactured for reducing the component cost.

In the present embodiment, an example that the relay lens 56 is constituted by a single lens is described, however, the configuration of the relay lens 56 is not limited thereto. For example, the relay lens 56 only has to be configured with the optical characteristic capable of relaying the incident entering the pair of the eccentrical lens 53 to the image sensor disposed at the distal end of the insertion portion of the endoscope 100. The relay lens 56 can be configured to be a single lens, and the relay lens 56 can also be configured by bonding a plurality of lens by the optical adhesive to form a cemented lens.

In the present embodiment, an example that the distal light-shielding portion 60 and the proximal light-shielding portion 61 have rectangle shapes is described, however, the configurations of the distal light-shielding portion 60 and the proximal light-shielding portion 61 are not limited thereto. For example, the distal light-shielding portion 60 and the proximal light-shielding portion 61 only have to be capable of suitably shielding the leak incident light, and thus the distal light-shielding portion 60 and the proximal light-shielding portion 61 can be formed in substantial circle shapes or other shapes. In a situation when the distal light-shielding portion 60 and the proximal light-shielding portion 61 are formed in other shapes except for the rectangle shapes, the widths of the distal light-shielding portion 60 and the proximal light-shielding portion 61 may be suitably determined such that the leak incident light can be suitably shielded with a reference of a straight line connecting the axes of the pair of the eccentrical lens 53 in the width direction of the adapter 1.

In the present embodiment, examples of the distal flare-cut stop 55 being D-cut processed, the proximal flare-cut stop 57 having the positioning portion 571, and the brightness stop 58 having the positioning portion 581 are described, however, they are not limited thereto. Such elements only have to be configured such that the rotations of the distal flare-cut stop 55, the proximal flare-cut stop 57, and the brightness stop 58 about the longitudinal axis L can be restricted when they are fixed to the main body 2 of the adapter 1, and the D-cut processing may be adopted, the positioning portion may be disposed, and the other shapes of the elements may be applied.

Second Embodiment

Figure 8:
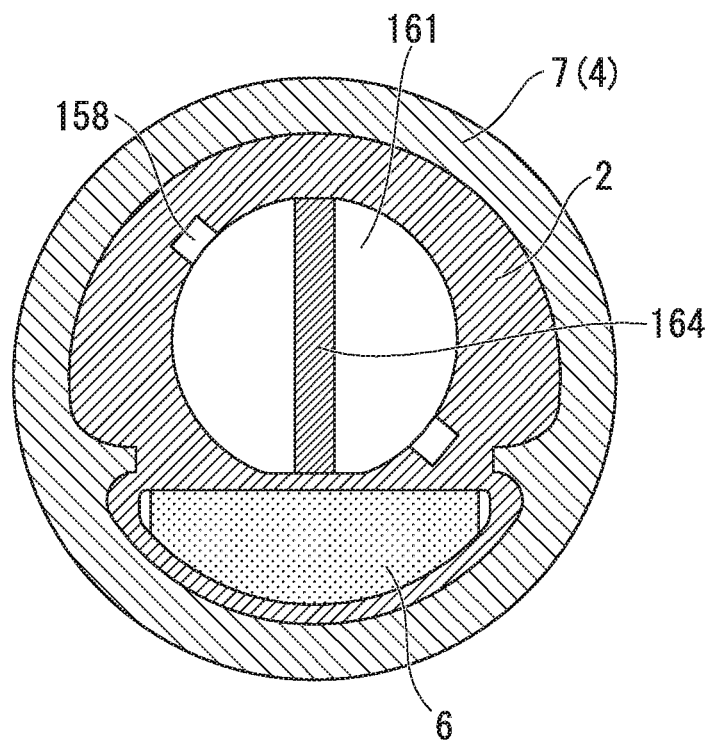
FIG. 8 is a VIII-VIII line sectional view of the FIG. 7.

Next, an optical adapter 10 for endoscope (hereinafter described as "adapter") according to a second embodiment of the present invention will be described by referring the figures. The same parts as those of the above-described embodiment are denoted with the same reference numerals and overlapping descriptions will be omitted, and only a difference will be described herewith. FIG. 7 is a view showing a configuration of the adapter 10 according to the present embodiment. FIG. 8 is a VIII-VIII line sectional view of the adapter 10 in the FIG. 7, and FIG. 8 is a view taken from the distal end of the adapter 10.

The adapter 10 according to the present embodiment and the adapter 1 according to the first embodiment are different in that a relay lens 156 according to the present embodiment is formed by bonding two lens using the optical adhesive. The adapter 10 according to the present embodiment has a distal light-shielding portion 162 formed by the vacuum vapor deposition, wherein the distal light-shielding portion 162 is disposed on a distal surface of a distal lens 160 of the relay lens 156 instead of the distal flare-cut stop 55 according to the first embodiment. The adapter 10 according to the present embodiment has a proximal light-shielding portion 163 formed by the vacuum vapor deposition, wherein the proximal light-shielding portion 163 is disposed on a proximal surface of a proximal lens 161 of the relay lens 156 instead of the proximal light-shielding flare-cut 57 according to the first embodiment. Furthermore, the adapter 10 according to the present embodiment has a middle light-shielding portion 164 formed by the vacuum vapor deposition on a distal surface of the proximal lens 161 of the relay lens 156.

Generally, the vacuum vapor deposition is one of well-known film-forming technologies. The vacuum vapor deposition is a film-forming technology in which the vapor deposition materials (metal materials such as aluminum, chromium, and the like) are heated in a high vacuum environment to cause the thermal vaporization of the vapor deposition materials such that the vapor deposition materials are vaporized into gas molecules and collide with the substrate, and thus the gas molecules are coated on the substrate to forma deposited thin film. Part of the surface of lens is coated by a metal fine particulate layer formed by the vacuum vapor deposition such that the leak incident light can be shielded as the same effects of the flare-cut stop disclosed in the first embodiment.

As shown in FIG. 7, the adapter optical system 15 of the adapter 10 according to the present embodiment has a cover glass 151, a pair of eccentrical lens 153, a focus adjustment sheet 154, a relay lens, and a brightness stop 158 in this order from the distal end side toward the proximal end side of the adapter 10. A metal fine particulate layer is formed on a proximal surface of the cover glass 151 by the vacuum vapor deposition as the visual-field stop. The relay lens 156 is configured by bonding the distal lens 160 and the proximal lens 161 using the optical adhesive. The shapes of the distal light-shielding portion 162 and the proximal light-shielding portion 163 can be determined by the same method as that of the distal light-shielding portion 60 and the proximal light-shielding portion 61 according to the first embodiment. That is, the shapes of the distal light-shielding portion 162 and the proximal light-shielding portion 163 are determined such that the leak incident light from the pair of the eccentrical lens 153 cannot reach the image sensor disposed at the distal end of the insertion portion of the endoscope.

Next, the middle light-shielding portion 164 according to the present embodiment will be described. As shown in FIG. 8, the distal lens 160 and the proximal lens 161 of the relay lens 156 according to the present embodiment are D-cut processed at the outer circumference respectively. When the relay lens 156 is assembled, the distal lens 160 and the proximal lens 161 are bonded by matching the D-cut processed portion of the distal lens 160 and the D-cut processed portion of the proximal lens 161. Then, the bonded relay lens 156 is fixed to the main body 2 based on the D-cut processed portions. Accordingly, the rotation of the relay lens 156 about the longitudinal axis L of the adapter 1 is restricted. In order to stably fix the relay lens 156 to the main body 2, the D-cut processed portion is preferably to be provided with a big dimension.

Figure 9:
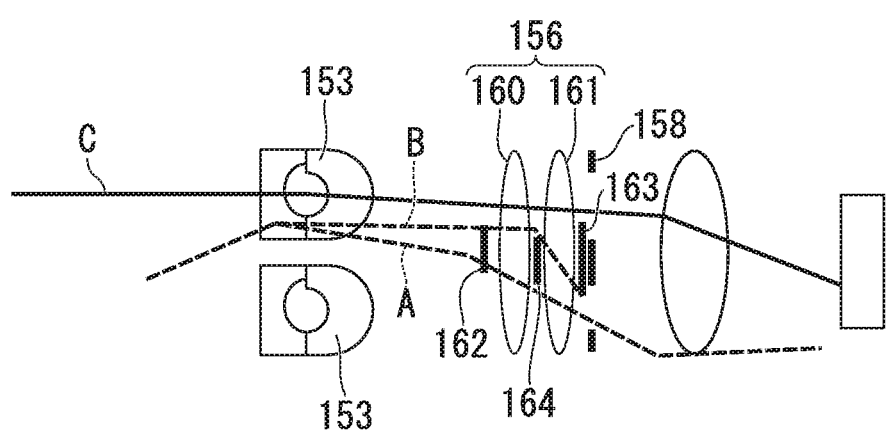
FIG. 9 is a schematic diagram showing a light-shielding principle of the optical adapter for an endoscope according to the second embodiment.

The middle light-shielding portion 164 according to the present embodiment is arranged in a direction substantially perpendicular to the D-cut processed portion of the proximal lens. The shape of the middle light-shielding portion 164 is determined to have a certain allowance for definitely shielding the possible optical path of the leak incident light through the pair of the eccentrical lens 153. In the adapter 10 according to the present embodiment, the middle light-shielding portion 164 is formed in a substantially rectangle shape. As a result, as shown in FIG. 9, in order to form an image on the image sensor, the necessary incident angle of the leak incident light B through the pair of the eccentrical lens 153 increases. In other words, the possibility of the incident of the leak incident light into the brightness stop decreases, and thus the leak incident light can be more definitely shielded.

According to the adapter 10 according to the present embodiment, compared to the first embodiment described above, the leak incident light can be more definitely shielded.

According to the adapter 10 according to the present embodiment, compared to the first embodiment described above, since the distal flare-cut stop 55 and the proximal flare-cut stop 57 are not necessary to be disposed such that the number of the elements can be reduced and the assembly becomes easier.

In the present embodiment, an example that the distal lens 160 and the proximal lens 161 of the relay lens 156 are D-cut processed is described, however, the configurations are not limited thereto. For example, a method of forming a projection as a positioning portion at each of the distal lens 160 and the proximal lens 161 using molded lens is possible. In such a case, corresponding to the positioning portions of the distal lens 160 and the proximal lens 161, a positioning portion may be formed in the main body 2, and the relay lens 156 only has to be configured such that the rotation of the relay lens 156 about the longitudinal axis L of the adapter 1 is restricted.

In the present embodiment, an example of forming the middle light-shielding portion 164 in the substantially rectangle shape is described, however, the configuration of the middle light-shielding portion 164 is not limited thereto. For example, when the middle light-shielding portion 164 is formed in a substantially circle shape, the widths of the distal light-shielding portion 162 and the proximal light-shielding portion 163 may be suitably determined such that the leak incident light through the adapter optical system 15 can be prevented from entering the brightness stop 158 with a reference of a straight line connecting the axes of the pair of the eccentrical lens 53 in the width direction of the adapter 10.

In the present embodiment, an example of forming the middle light-shielding portion 164 by the vacuum vapor deposition is described, however, the configuration of the middle light-shielding portion 164 is not limited thereto. For example, the middle light-shielding portion 164 may be formed by painting or the like. Furthermore, in a situation in which the leak incident light can be efficiently shielded by the distal light-shielding portion 162 and the proximal light-shielding portion 163, the middle light-shielding portion 164 may not be formed.

Although preferred embodiments of the present invention have been described above by referring to the figures, the present invention is not limited to the embodiments. Additions, omissions, substitutions and other changes in the structure are possible without departing from the spirit of the present invention. The present invention is not limited by the foregoing description but is limited only by the scope of the appended claims.

For example, the adapter according to the present invention may be configured to have a distal flare-cut stop having a distal light-shielding portion, a proximal flare-cut stop having a proximal light-shielding portion, and a middle light-shielding portion formed by the vacuum vapor deposition.

What is claimed is:

1. An optical adapter for an endoscope configured to be removably attached to a distal end of an insertion portion of the endoscope, the optical adapter comprising:
    a plurality of incident optical systems eccentrically disposed with each other, an optical axis of each of the plurality of incident optical systems being spaced away from an axis of the optical adapter with an interval;
    a brightness stop including a plurality of apertures, the plurality of apertures corresponding to the plurality of incident optical systems respectively;
    a relay lens configured to relay incident light entering each of the plurality of incident optical systems to a corresponding aperture among the plurality of apertures;
    a distal light-shielding portion disposed distally relative to the relay lens; and
    a proximal light-shielding portion disposed proximally relative to the relay lens,
    wherein the plurality of incident optical systems, the relay lens, and the brightness stop are disposed in this order from a distal end side toward a proximal end side of the optical adapter along an incident direction of the incident light.

2. The optical adapter according to claim 1, further comprising:
    a distal flare-cut stop disposed distally relative to the relay lens,
    wherein the distal light-shielding portion is disposed at the distal flare-cut stop.

3. The optical adapter according to claim 1, wherein the distal light-shielding portion is formed on a distal surface of the relay lens.

4. The optical adapter according to claim 1, further comprising:
    a distal flare-cut stop disposed distally relative to the relay lens, and
    a proximal flare-cut stop disposed proximally relative to the relay lens,
    wherein the distal light-shielding portion is disposed at the distal flare-cut stop, and
    wherein the proximal light-shielding portion is disposed at the proximal flare-cut stop.

5. The optical adapter according to claim 1,
    wherein the distal light-shielding portion is formed on a distal surface of the relay lens, and
    wherein the proximal light-shielding portion is formed on a proximal surface of the relay lens.

6. The optical adapter according to claim 1, further comprising:
    a lens frame configured to hold the plurality of incident optical systems; and
    an adapter main body configured to hold the relay lens,
    wherein the lens frame is abutted by the adapter main body such that the lens frame and the adapter main body are engaged with each other to determine positions of the plurality of incident optical systems with respect to the relay lens.

7. The optical adapter according to claim 1, wherein the relay lens is a cemented lens formed by combining a distal lens and a proximal lens.

8. An optical adapter for an endoscope configured to be removably attached to a distal end of an insertion portion of the endoscope, the optical adapter comprising:
    a plurality of incident optical systems which are eccentrically disposed with each other, an optical axis of each of the plurality of incident optical systems being spaced away from an axis of the optical adapter for an endoscope with an interval;
    a brightness stop which includes a plurality of apertures, the plurality of apertures corresponding to the plurality of incident optical systems respectively;
    a relay lens which is configured to relay incident light entering each of the plurality of incident optical systems to the corresponding aperture among the plurality of apertures of the brightness stop; and
    a distal light-shielding portion which is disposed in the vicinity of the relay lens at a distal side of the relay lens such that the distal light-shielding portion is configured to shield the incident light to the center of the relay lens,
    wherein the plurality of incident optical systems, the relay lens, and the brightness stop are disposed in this order from a distal end side toward a proximal end side of the optical adapter for an endoscope along an incident direction of the incident light, and
    the distal light-shielding portion contacts a distal surface of the relay lens.

9. The optical adapter according to claim 8, wherein the distal light-shielding portion is formed on the distal surface of the relay lens.

* * * * *